United States Patent [19]

Baker et al.

[11] Patent Number: 4,687,660
[45] Date of Patent: Aug. 18, 1987

[54] PHARMACEUTICAL DELIVERY SYSTEM

[75] Inventors: Richard W. Baker, Mountain View, Calif.; James W. Brooke, Sisters, Oreg.

[73] Assignee: Burroughs Wellcome Co., Research Triangle Park, N.C.

[21] Appl. No.: 640,951

[22] Filed: Aug. 15, 1984

[30] Foreign Application Priority Data

Aug. 16, 1983 [GB] United Kingdom ................. 8322007

[51] Int. Cl.$^4$ ......................... A61K 9/22; A61K 9/32; A61K 31/60
[52] U.S. Cl. ................................... 424/465; 604/890; 604/892
[58] Field of Search .................... 424/19, 22, 32, 35, 424/15, 33; 604/890, 892

[56] References Cited

U.S. PATENT DOCUMENTS

| | | | |
|---|---|---|---|
| 2,011,587 | 8/1935 | Miller | 424/22 |
| 2,987,445 | 6/1961 | Levesque | 424/22 |
| 3,538,214 | 11/1970 | Polli et al. | 424/22 |
| 3,773,920 | 11/1973 | Nakamoto et al. | 424/19 |
| 4,016,880 | 4/1977 | Theeuwes et al. | 424/35 |
| 4,060,598 | 11/1977 | Groppenbächer et al. | 424/33 |
| 4,173,626 | 11/1979 | Dempski et al. | 424/22 |
| 4,309,405 | 1/1982 | Guley et al. | 424/19 |
| 4,439,194 | 3/1984 | Harwood et al. | 604/890 |
| 4,439,196 | 3/1984 | Higuchi | 604/890 |
| 4,519,801 | 5/1985 | Edgren | 604/890 |
| 4,539,198 | 9/1985 | Powell et al. | 424/19 |
| 4,557,925 | 12/1985 | Lindahl et al. | 424/19 |

FOREIGN PATENT DOCUMENTS

| | | |
|---|---|---|
| 280478 | 4/1970 | Austria . |
| 305498 | 2/1973 | Austria . |
| 1326995 | 8/1973 | United Kingdom . |
| 2025227 | 1/1980 | United Kingdom . |

OTHER PUBLICATIONS

Journal of Pharmaceutical Sciences, Jul. 1983, vol. 72, No. 7, pp. 772-775.

*Primary Examiner*—Ronald W. Griffin
*Attorney, Agent, or Firm*—Donald Brown

[57] ABSTRACT

A composition for use in an aqueous environment which comprise a formulation containing a water-soluble pharmaceutically beneficial agent, a water-insoluble, water-permeable film coating surrounding the formulation, and particulate, water-soluble, pore-forming material dispersed within the film coating.

6 Claims, 3 Drawing Figures

PHARMACEUTICAL DELIVERY SYSTEM

FIELD OF THE INVENTION

This invention relates to a device which provides the controlled, continuous dispensing of a water-soluble beneficial agent for a predetermined period of time. Moreover, the invention relates to such a device powered by an osmotic pumping mechanism, to the preparation of such a device and to the use of such a device in the medical, veterinary and other fields.

BACKGROUND OF THE INVENTION

Systems for the delivery of pharmaceutically beneficial agents are well known in the art. Dispensing systems which deliver their contents by diffusion through a permeable polymer coating or wall are well known but suffer from severe limitations. For example, many pharmaceutically beneficial agents cannot be delivered from such diffusion controlled devices. In many instances permeation rates through the permeable polymer coating are inadequate to provide useful concentrations of the beneficial agent. In many others, the beneficial agent has such a high molecular weight that it will not diffuse through the polymer coating.

Also well known are delivery systems which operate by means of an osmotic pumping mechanism. In a typical delivery system of this type the beneficial agent is contained within a continuous, semipermeable film, e.g. a capsule or a film coating, having a hole of predetermined size drilled therethrough. In operation the delivery system is placed in the appropriate aqueous environment, e.g. the stomach or cul-de-sac of the eye, whereupon it imbides water through the semi-permeable film, thereby dissolving at least in part the contents of the delivery system. This causes an increase in the internal (osmotic) pressure, which results in the dissolved contents being continuously pumped out of the delivery system through the hole at a controlled rate over a predetermined period of time.

The devices taught in the art have a number of deficiencies. They are, in most case, complex devices having multiple parts or requiring special fabrication steps. For example, many require the drilling of a hole through the film coating of each device. Consequently, the delivery system itself is relatively expensive to fabricate and contributes substantially to the final cost of the product.

Prior art devices each having a single passageway through which their dissolved contents are delivered have other disadvantages. When the beneficial agent contained and delivered by such a device is irritating to the biological tissue in the region in which the device is used, local tissue irritation could be a problem at the locus of delivery of the agent, i.e. in the vicinity of the hole through which the concentrated agent is pumped.

Alternatives to drilling individual holes through the semipermeable film have been disclosed. For example, the use of a friable, inexpandable wall has been described which fractures when it imbibes water to provide cracks and fissures through which the contents are then delivered. Passageways provided by erosion of bioerodible fibers incorporated in the wall of the delivery device have also been described.

There is a very large body of art describing the various delivery systems. The U.S. patents below are cited as representative of the controlled delivery system art: U.S. Pat. Nos. 3,845,770; 3,916,899; 4,016,880; 4,160,452; and 4,200,098.

SUMMARY OF THE INVENTION

The present invention provides a method and means for dispensing in a controlled, continuous manner therapeutically effective amounts of water-soluble drugs for a predetermined period of time to achieve a predetermined useful effect in animals, especially mammals, including in particular human beings. In one aspect a core comprising the desired water-soluble beneficial agent together with any desired excipient(s) including osmotic enhancing agents is film coated with a solution of a water-insoluble, water-permeable polymer, a water-permeability-modifying agent (if desired), and a water-soluble, polymer-solvent-insoluble, particulate, pore-forming material.

When the pore-forming material is soluble in the solvent used to dissolve the polymer, it can be suspended in a pore-forming material non-solvent which is compatible with the polymer solution. The polymer solution and the pore-forming material suspension can then be separately but simultaneously applied, as by spray coating in a pan coater or fluidized bed.

In another aspect of the present invention there is provided a method of simply and reproducibly mass producing osmotically driven, controlled release devices for dispensing water-soluble beneficial agents.

It is contemplated that the controlled release device of the present invention also has utility in non-animal environments such as in agriculture (e.g., for the controlled delivery of fertilizers, soil trace minerals or elements, fungicides, herbicides and the like) or other environments in which it would come into contact with water from time to time or continuously.

When the device of the present invention is used, e.g., by oral administration to a human being, it comes into contact with an aqueous environment. Water is imbibed through the semi-permeable film coating, in the process leaching out the water-soluble particles in the film coating. The imbibed water dissolves the water-soluble beneficial agent as well as osmotic enhancing agents present. This sets up the osmotic gradient which actively brings in water through the semi-permeable membrane thereby increasing the pressure inside the device, resulting in the saturated (or partially saturated) solution of the beneficial agent being pumped out through the micropassageways created by the water dissolving the pore-forming, watersoluble particles imbedded in the film coating of the device.

BRIEF DESCRIPTION OF THE DRAWINGS

The drawings are not drawn to scale. They are set forth to illustrate the invention, and are as follows.

In the drawings and specification, like parts are identified by like numbers.

DETAILED DESCRIPTION OF THE DRAWINGS

Figure 1:
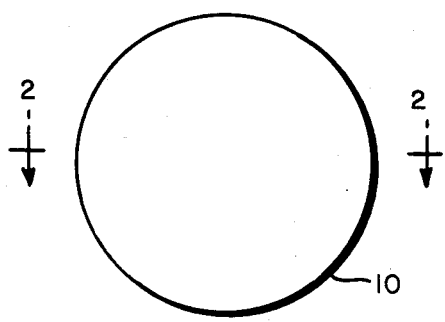
FIG. 1 is a view of a controlled release tablet for the delivery of a beneficial agent.

The drawings illustrated here are intended to schematically represent the controlled delivery device of the invention and are not to be considered limiting. FIG. 1 represents one example of the delivery device, indicated by the numeral 10, a tablet for oral administration to an animal.

Figure 2A:
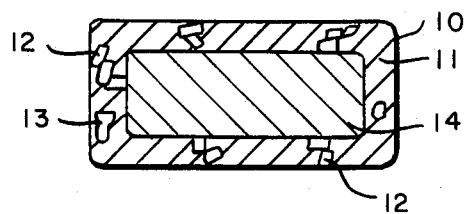
FIG. 2(a) is a sectional view taken along line 2—2 schematically illustrating the functional structure of the tablet as manufactured, i.e. before use.
Figure 2B:
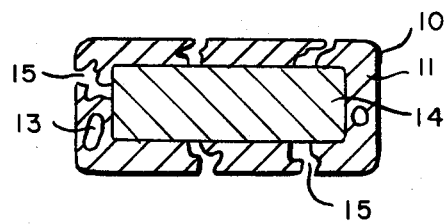
FIG. 2(b) is the same sectional view as depicted in FIG. 2(a) schematically illustrating the functional structure of the tablet after the pore-forming material has been dissolved during use.

In FIG. 2(a) the tablet 10 of FIG. 1 is depicted in cross-section illustrating the structure of the tablet as manufactured. Tablet 10 comprises a water-permeable, water-insoluble film coating 11 which may contain in the film coating plasticizers and/or water-permeability-modifying agents and which has dispersed therein particulate, pore-forming material 12 and 13. The individual particles of pore-forming material 12 are in substantial contact with one another across the thickness of film 11 and, when the tablet 10 is used for its intended use, are dissolved out to form the pores 15 therethrough as shown in FIG. 2(b). The individual particles of pore-forming material 13 are not in contact with one another across the thickness of film 11 and, when the tablet 10 is used, do not form pores through film 11. The film coating 11 encompasses a core 14 which comprises at least one water-soluble beneficial agent. Core 14 may contain other desired excipients including osmotic enhancing agents when it is desired to increase the osmotic pressure developed within the tablet 10 when in use.

FIG. 2(b) depicts the same cross-section as shown in FIG. 2(a) after sufficient exposure to its environment of use to dissolve the pore-former particles.

DETAILED DESCRIPTION OF THE INVENTION

The novel controlled delivery device of the present invention is simple in construction, permitting efficient mass production by conventional techniques. It is simple in operation, being no more complex to use than a conventional tablet or capsule.

Water-insoluble, water-permeable polymers suitable for forming the film coating of the device of the present invention include homopolymers and copolymers which are semipermeable. By semipermeable is herein meant permeable to solvent but not to solute, i.e., permeable to water but not permeable to the beneficial agent or osmotic enhancing agent dissolved therein. Suitable polymeric materials include cellulose esters such as mono-, di- and triacylates including mixed esters, cellulose ethers such as ethyl cellulose, nylons, polycarbonates, poly(dialkylsiloxanes), poly(methacrylic acid) esters, poly(acrylic acid) esters, poly(phenylene oxides), poly(vinyl alcohols), aromatic nitrogen-containing polymers, polymeric epoxides, regenerated cellulose and other membrane-forming materials suitable for use in reverse osmosis or dialysis application. Some examples of such suitable film-forming materials include cellulose acetate, cellulose diacetate, cellulose triacetate, cellulose propionate, cellulose acetate butyrate, cellulose acetate propionate, cellulose tripropionate, ethyl cellulose, nylon 6 and the like. The film coating, in addition to being semipermeable, must not adversely affect the beneficial agent or the animal receiving the device. The thickness of the film coating is desirably 10 to 500 $\mu$m, preferably 25 to 250 $\mu$m.

Plasticizers may be used in the semipermeable polymeric film coating of the present invention. Typical plasticizers which may be used include esters such as the phthalates, phosphates, citrates, adipates, tartrates, sebacates, succinates, glycolates, glycerolates, benzoates and myristates, sulfonamides and the like. Specific examples include dimethyl phthalate, dipropyl phthalate, di-(2-ethylhexyl) phthalate, tributyl phosphate, triacetyl phosphate, and tributyl citrate. The plasticizer must be compatible with the other materials of the film coating. It should also have a high degree of permanence, i.e., it should remain in the polymeric film and not migrate to the surface to an appreciable extent. It should also have no adverse effect on the beneficial agent or the animal receiving the device.

The term "water-permeability-modifying agent" as used herein means a compound or material which when added to the semipermeable film-forming material modifies the water permeability of the film produced therefrom, enhancing or increasing its permeability to water. Permeability-modifying agents include the poly(alkylene glycols), esters and polyesters of poly(alkylene glycols), polyhydric alcohols and esters and polyesters of polyhydric alcohols. Specific examples of suitable water-permeability-modifying agents include poly(ethylene glycols) 300, 400, 600, 1500 and 1540, poly(propylene glycol), 1,3-butyleneglycol, glycerine, ethylene glycol dipropionate, ethylene glycol butyrate and the like.

The pore-forming material must be particulate in nature, with a maximum particle size preferably not exceeding about 500 $\mu$m in its longest dimension and an average particle size from about 1 $\mu$m to about 300 $\mu$m, more preferably having an average particle size from about 5 $\mu$m to about 100 $\mu$m. It must be soluble in water or aqueous media and insoluble in the organic solvent in which the polymeric film-forming material is dissolved during the film-coating process. Suitable pore-forming materials include the water-soluble sugars, e.g., lactose, sucrose, sorbitol and mannitol, and water-soluble salts, e.g., sodium carbonate, sodium chloride, calcium chloride, potassium chloride and sodium sulfate, and the like. When the device of this invention is intended for pharmaceutical use, the poreforming material should be pharmaceutically acceptable. A portion of the beneficial agent may be used as the pore-forming material, and in certain formulations this may be preferred.

Osmotic enhancing agents are water-soluble materials having a high molar water solubility (high water solubility on a molar basis) which are capable of achieving in solution an osmotic pressure greater than that of the aqueous environment of the device of this invention when in use. Suitable osmotic enhancing agents include sugars, e.g. sucrose, lactose, fructose, mannitol and the like; salts, e.g. sodium chloride, potassium chloride, sodium carbonate and the like; as well as other water-soluble organic or inorganic compounds. When used in devices for human or veterinary use the osmotic enhancing agents should be pharmaceutically acceptable.

The delivery devices of the present invention are manufactured by standard techniques. In one embodiment tablets, which are suitable for oral administration to a mammal, containing the desired beneficial agent together with standard excipients as well as osmotic-enhancing agents, if desired, are prepared in a conventional manner. They are then coated with a controlled-porosity, water-permeable film by spraying for example in a rotating pan coater or fluidized-bed coater with a solution of the film-forming polymer, plasticizer (if desired) and permeability-modifying agent (if desired)

containing the poreforming material suspended therein until the desired film thickness is achieved.

Beneficial agents suitable for use in the devices of this invention must be water soluble and produce a beneficial effect when delivered from the device. Such beneficial agents include pharmaceutical agents for use in human and veterinary medicine, nutrients, pesticides, insecticides, fungicides, herbicides, algicides, vitamins, fertilizers, soil trace minerals or elements and the like. Specific examples include d-pseudoephedrine hydrochloride; bupropion hydrochloride; soluble potassium salts such as potassium chloride, potassium citrate, potassium gluconate, and the like; chlorpheniramine maleate; propranolol hydrochloride; cimetidine; phenylpropanolamine hydrochloride; dextromethorphan hydrobromide; ascorbic acid; aspirin; acetaminophen, codeine salts; methomyl; copper sulfate; ammonium nitrate and the like.

When used in human or veterinary medicine the devices of this invention may be administered in any appropriate manner. For example, administration by oral, subcutaneous implantation, suppository insertion, inter alia may be employed with these devices.

The following examples further illustrate but should not be construed as limiting the invention.

EXAMPLE 1

Tablets containing 100 mg bupropion hydrochloride and 500 mg lactose were prepared using a conventional tablet press. Fifty tablets were placed in a miniature pan coater. A polymer solution was prepared by dissolving cellulose acetate (CA 383-40 from Eastman Chemical Products, Inc., Kingsport, Tenn.) and poly(ethylene glycol) (Polyglycol E-400 from Dow Chemical Co., Midland, Mich.) in acetone and adding impalpable lactose (particle size: 2-20 $\mu$m) to give a mixture containing cellulose acetate: poly(ethylene glycol): lactose in the weight % ratio of 40:40:20 and a total solids content of 50 g/L. The polymer mixture was sprayed onto the tablets in the pan coater to give film-coated tablets having a film coating weighing 27 mg each when dried.

Drug release rates were determined for the tablets by placing them in simulated gastric buffer (pH 1.5) at 37° C. and periodically measuring the bupropion hydrochloride concentration in the buffer. After 2 hr., about 45% of the bupropion hydrochloride was released; after 4 hr., about 70%; and after 6 hr., about 90%.

EXAMPLE 2

Tablets containing 100 mg bupropion hydrochloride and 500 mg lactose were prepared using a conventional tablet press. Fifty tablets were placed in a miniature pan coater. A polymer solution was prepared by dissolving cellulose acetate (CA 383-40) and poly (ethylene glycol) (Polyglycol E-400) in acetone and adding impalpable lactose to give a mixture containing cellulose acetate: poly(ethylene glycol): lactose in the weight % ratio of 67:13:20 and a total solids content of 50 g/L. The polymer mixture was sprayed onto the tablets in the pan coater to give film-coated tablets having film coating weighing 35 mg each when dried.

Drug release rates were determined for the tablets by placing them in simulated gastric buffer (pH 1.5) at 37° C. and periodically measuring the bupropion hydrochloride concentration of the buffer. After 2 hr., about 10% of the bupropion hydrochloride was released; after 4 hr., about 25%; after 6 hr., about 40%; and after 8 hr., about 55%.

EXAMPLE 3

Tablets containing 120 mg d-pseudoephedrine hydrochloride, 5 mg triprolidine hydrochloride, 125 mg lactose, and 28 mg starch were prepared using a conventional tablet press. Fifty tablets were placed in a miniature pan coater. A polymer solution was prepared by dissolving cellulose acetate (CA 398-10 from Eastman Chemical Products., Inc., Kingsport, Tenn.) and poly(ethylene glycol) (Polyglycol E-400) in acetone and adding powdered sodium carbonate (particle size: 30-200 $\mu$m) to give a mixture containing cellulose acetate: poly(ethylene glycol): sodium carbonate in the weight % ratio of 40:40:20 and a total solids content of 50 g/L. The polymer mixture was sprayed onto the tablets in the pan coater to give film-coated tablets having a film coating weighing 64 mg each when dried.

Drug release rates were determined for the tablets by placing them in simulated gastric buffer (pH 1.5) at 37° C. and periodically measuring the drug concentration. After 1 hr., about 33% of the d-pseudoephedrine hydrochloride and 32% of the triprolidine hydrochloride was released; after 2 hr., about 53% of each drug was released; after 3 hr., about 71% and 74%, respectively; and after 4 hr., about 97% and 85%, respectively.

It will be appreciated from the foregoing that what we will claim may comprise any novel feature described herein, principally, but not exclusively, for example:

(a) A delivery system for the controlled release of a water-soluble beneficial agent comprising (i) a core containing said agent and (optionally) an osmotic enhancing agent and excipients, and (ii) encompassing said core a water-insoluble, water-permeable, polymeric film containing discrete, water-soluble particles which during use of the system dissolve in the aqueous environment thereof to leave pores in said film, and (optionally) containing a water-permeability-enhancing amount of a water-permeability-modifying agent and a plasticizer:

(b) A method of preparing a device as defined in (a) above substantially as hereinbefore described;

(c) A method of delivering a water-soluble beneficial agent in a controlled, continuous manner using a device as defined in (a) above.

What we claim is:

1. A tablet comprising a core containing the admixture of a water-soluble medicine and a water-soluble osmotic enhancing agent in an amount by weight about equal to or greater than the weight of the medicine, said core having a water-insoluble, water-permeable coating surrounding said core, said coating containing particulate, water-soluble, pore-forming material dispersed therein.

2. The tablet of claim 1 in which the osmotic enhancing agent is a pharmaceutically acceptable water-soluble sugar or salt.

3. The tablet of claim 2 in which the pore forming material dispersed in the coating is a pharmaceutically acceptable water-soluble sugar or salt.

4. The tablet of claim 1 in which the osmotic enhancing agent and the pore-forming material are both lactose.

5. A composition comprising a core containing the admixture of a water-soluble medicine and a water-soluble osmotic enhancing agent in an amount by weight about equal to or greater than the weight of the medicine, said core having a water-insoluble, water-permeable coating surrounding said core, said coating containing particulate, water-soluble, pore-forming material dispersed therein and an agent to increase the water permeability of the coating dispersed therein.

6. The composition of claim 5 wherein the water permeability increasing agent is polyethylene glycol.

* * * * *